US010166373B2

(12) United States Patent
Ward et al.

(10) Patent No.: US 10,166,373 B2
(45) Date of Patent: Jan. 1, 2019

(54) ELASTIC TIP FOR AN ADJUSTABLE LENGTH ANGIOPLASTY BALLOON SHEATH

(71) Applicant: Biosensors International Group, Ltd., Hamilton (BM)

(72) Inventors: Roseann Ward, Fremont, CA (US); Eugene Serina, Fremont, CA (US); Emilio Crisolo, Union City, CA (US)

(73) Assignee: Biosensors International Group, Ltd., Hamilton (BM)

( * ) Notice: Subject to any disclaimer, the term of this patent is extended or adjusted under 35 U.S.C. 154(b) by 186 days.

(21) Appl. No.: 14/923,809

(22) Filed: Oct. 27, 2015

(65) Prior Publication Data

US 2016/0121087 A1    May 5, 2016

Related U.S. Application Data

(60) Provisional application No. 62/073,558, filed on Oct. 31, 2014.

(51) Int. Cl.
*A61M 25/10* (2013.01)
*A61M 25/00* (2006.01)

(52) U.S. Cl.
CPC .......... *A61M 25/104* (2013.01); *A61M 25/10* (2013.01); *A61M 2025/0024* (2013.01);
(Continued)

(58) Field of Classification Search
CPC ................ A61M 25/10; A61M 25/104; A61M 2025/0024; A61M 2025/1043; A61M 2025/1068; A61M 2025/1079; A61M 2025/1081; A61M 2025/1084; A61M 2025/1093
See application file for complete search history.

(56) References Cited

U.S. PATENT DOCUMENTS 5,447,503 A * 9/1995 Miller ............... A61M 25/0068
604/528
5,735,859 A    4/1998 Fischell et al.
(Continued)

FOREIGN PATENT DOCUMENTS

WO         9619256 A1    6/1996

OTHER PUBLICATIONS

PCT/US2015/057506, "International Search Report and Written Opinion", dated Dec. 29, 2015, 8 pages.
(Continued)

*Primary Examiner* — Robert Lynch
(74) *Attorney, Agent, or Firm* — Kilpatrick Townsend & Stockton LLP

(57) ABSTRACT

The present disclosure describes an angioplasty balloon catheter having a retractable sheath and a flexible tip attached to the distal end of the sheath. The flexible tip is made of an elastomeric plastic that is capable of returning to its original shape after being expanded multiple times. The tip allows for the sheath to be retractable and the balloon inflated multiple times to treat or expand different locations within the vessel. Because the tip returns to its original shape each time, the tip is less likely to damage the vessel wall when the sheath is repositioned in the vessel, and also is easier to retract through a guide-catheter.

17 Claims, 3 Drawing Sheets

(52) U.S. Cl.
CPC .............. *A61M 2025/1043* (2013.01); *A61M 2025/1068* (2013.01); *A61M 2025/1079* (2013.01); *A61M 2025/1081* (2013.01); *A61M 2025/1084* (2013.01); *A61M 2025/1093* (2013.01)

(56) References Cited

U.S. PATENT DOCUMENTS

| | | | |
|---|---|---|---|
| 5,843,027 | A | 12/1998 | Stone et al. |
| 5,860,963 | A * | 1/1999 | Azam .................. A61L 2/08 138/124 |
| 6,344,045 | B1 | 2/2002 | Lim et al. |
| 6,979,343 | B2 * | 12/2005 | Russo .................. A61F 2/013 606/200 |
| 7,901,425 | B2 | 3/2011 | Petrick et al. |
| 2004/0215314 | A1 | 10/2004 | Kantor et al. |
| 2007/0073269 | A1 * | 3/2007 | Becker ................ A61M 3/0295 604/509 |
| 2007/0225659 | A1 | 9/2007 | Melsheimer et al. |
| 2013/0096604 | A1 | 4/2013 | Hanson et al. |
| 2014/0012193 | A1 * | 1/2014 | Qiu .................. A61M 25/0009 604/96.01 |
| 2014/0018837 | A1 * | 1/2014 | Zhou .................. A61M 25/09 606/194 |

OTHER PUBLICATIONS

EP15853851.2 , "Extended European Search Report", dated Mar. 22, 2018, 9 pages.

SG11201703485X , "Written Opinion", dated Feb. 21, 2018, 5 pages.

* cited by examiner

ELASTIC TIP FOR AN ADJUSTABLE LENGTH ANGIOPLASTY BALLOON SHEATH

CROSS-REFERENCES TO RELATED APPLICATIONS

This application claims the benefit under 35 U.S.C. § 1.119(e) of U.S. provisional Application No. 62/073,558, filed Oct. 31, 2014, the entire contents of which are incorporated by reference herein.

BACKGROUND OF THE INVENTION

Balloon catheters are commonly used in angioplasty procedures to expand vessels in the body, for example, blood vessels that are narrowed due to the deposition of plaque during arteriosclerosis. Some balloon catheters have a slidable sheath over the balloon to adjust the length of the balloon that is inflated. In many angioplasty procedures, the balloon or a portion thereof is inflated and deflated multiple times, depending on the size or number of regions in the vessel that need to be expanded. Thus, the sheath can be partially retracted multiple times during a single procedure, corresponding to each time the balloon is expanded. Balloon catheters typically have a flexible tip located at the distal end of the sheath to prevent damage to the vessel during insertion of the catheter, for example, over a guide wire.

In some procedures, the balloon or a portion thereof is passed through the flexible tip prior to inflation. The flexible tip flares out in the distal direction as the balloon is inflated. Thus, the flexible tip can be permanently deformed during expansion and deflation of the balloon. The deformed shape of the tip may cause damage to the vessel wall when the sheath is advanced in or retracted from the vessel, and may also make it more difficult to retract the sheath into a guide catheter. The present disclosure provides a solution to this problem by providing a flexible tip that returns to its original shape after multiple balloon expansions.

BRIEF SUMMARY OF THE INVENTION

The present application provides an elastomeric distal tip for an adjustable length angioplasty balloon catheter sheath. The distal tip provides the unexpected advantage of returning to its original shape, or substantially its original shape, after balloon expansion and deflation, which helps prevent trauma to the vessel when the sheath is repositioned in the vessel.

In one aspect, the elastomeric distal tip is attached to the distal end of an axially moveable retractable sheath that covers an inflatable balloon located at a distal end portion of the catheter. In some embodiments, the distal tip comprises an elastomeric plastic having a tensile strength of about 41 MPa to 50 MPa (megapascals), and a flexural modulus of between about 0.04 and 0.10 GPa (gigapascals). In some embodiments, the distal tip has a wall thickness of about 140 microns to about 191 microns. The distal portion of the retractable sheath is positioned concentrically around the inflatable balloon, such that the sheath surrounds the circumference of the folded (uninflated) balloon.

In another aspect, an angioplasty balloon catheter is provided, the catheter comprising an axially moveable retractable sheath and a distal tip attached to a distal end of the sheath, where the distal portion of the retractable sheath is positioned concentrically around an inflatable balloon. The distal tip of the sheath comprises an elastomeric plastic having a tensile strength of 41 MPa to 50 MPa, a flexural modulus of between 0.04-0.10 GPa (gigapascals) and a thickness of 140 microns to 191 microns.

In some embodiments, the distal tip is an elastomeric plastic comprising a copolymer of polyether and polyamide. In some cases, the distal tip is about 1.0 to 1.5 mm in axial length. The distal tip can be frustroconical in shape, having a greater diameter proximal end and a smaller diameter distal end. In some embodiments, the distal tip tapers in a distal direction (e.g., from the greater diameter proximal end to the smaller diameter distal end). In some embodiments, the distal tip comprises a lumen extending in a longitudinal direction from the proximal end to the distal end.

In some cases, the distal tip comprises an annular marker band disposed or located at the proximal end of the tip. The marker band typically has an inside diameter that is greater than the uninflated (folded) diameter of the balloon that is located on the distal end portion of the catheter. One function of the marker band is to help prevent the inflatable balloon from opening prematurely, for example, prior to balloon expansion by a cardiologist. The marker band can also be configured to help prevent the distal tip from over-expanding during balloon inflation. In some embodiments, the marker band is about 0.04 inches in axial length. In some embodiments, the lumen of the distal tip has an axial (or inside) diameter that is at least 0.01 inches less than the inside diameter of the marker band.

In another aspect, a method for treating a vessel in a subject in need of treatment is provided. In some embodiments, the method comprises:
(a) positioning a balloon catheter in a vessel of the subject;
(b) extending an inflatable balloon or a portion thereof through a lumen of the distal tip;
(c) expanding the balloon or portion thereof to come in contact with a vessel wall;
(d) deflating the balloon; and
(e) retracting the deflated balloon through the lumen of the distal tip;
wherein the distal tip returns to its original shape after deflation of the balloon.

If the vessel has more than one lesion that needs treatment, the catheter can be repositioned at the appropriate location in the vessel without retracting the catheter from the subject, and steps (b)-(e) above are repeated. The distal tip returns to substantially its original shape after each deflation of the balloon. Thus, the present disclosure provides a distal tip having unexpected advantages over the art.

BRIEF DESCRIPTION OF THE DRAWINGS

FIG. 1 illustrates one embodiment of a distal tip described herein.

DEFINITIONS

Figure 1A:
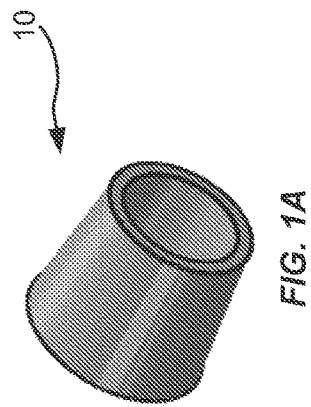
FIG. 1(A) shows an isometric view.

Unless defined otherwise, technical and scientific terms used herein have the same meaning as commonly understood by a person of ordinary skill in the art. The term "a" or "an" is intended to mean "one or more." The term "comprise" and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

The term "about," when modifying any amount, refers to the variation in that amount typically encountered by one of skill in the art, i.e., in the field of angioplasty balloon catheter design. For example, the term "about" refers to the normal variation encountered in measurements for a given analytical technique, both within and between batches or samples. Thus, the term about can include variation of 1-10% of the measured value, such as 1%, 2%, 3%, 4%, 5%, 6%, 7%, 8%, 9% or 10% variation. The amounts disclosed herein include equivalents to those amounts, including amounts modified or not modified by the term "about."

The term "elastomeric" or "elastomeric plastic" refers to a material, usually a polymer, having both viscosity and elastic properties. A thermoplastic elastomer is a polymer, copolymer, or mixture of polymers comprising materials with both thermoplastic and elastomeric properties. Examples of thermoplastic elastomers include polyether block amides, a type of block copolymer. According to the IUPAC, a block copolymer is defined as a portion of a macromolecule, comprising many constitutional units, that has at least one feature which is not present in the adjacent portions. See, McNaught, A. D. and Wilkinson, A. (1996). "Glossary of basic terms in polymer science (IUPAC Recommendations 1996)". *Pure and Applied Chemistry* 68: 2287-2311. Block copolymers are typically produced by polycondensation of a carboxylic acid polyamide with an alcohol termination polyether (such as Polytetramethylene glycol (PTMG), or PEG). The general chemical structure of a block polymer is:

HO—(CO-PA-CO—O-PE-O)$_n$—H

The term includes a polymer comprising a flexible polyether and a rigid polyamide.

The term "tensile strength" refers to the maximum amount of force or stress required to stretch or pull a material to the point where it breaks.

The term "flexural modulus" refers to how a material will strain and deform when force is applied to the material. It refers to the ratio of stress to strain in flexural deformation, or the tendency for a material to bend, and is determined from the slope of a stress-strain curve produced by a flexural test. The units are force per area. On example of a flexural test is the ASTM D 790.

The term "frustoconical" refers to the shape of a cone with the narrow end, or tip, removed. It is also defined as having the shape of a frustum of a cone, i.e., a cone whose tip is truncated by a plane parallel to its base.

The term "substantially" refers to an amount, value or characteristic that is similar, nearly identical, or equivalent to the amount, value or characteristic of the term it modifies. For example, the term "substantially original shape" when referring to the elastomeric distal tip described herein refers to a shape that is similar or nearly identical to the original shape of the tip before balloon expansion. For example, "substantially original shape" can refer to a shape that is within plus or minus 10%, 5%, or 1% of the diameter (both proximal end and distal end) and/or length of the distal tip before balloon expansion (either the first balloon expansion or the previous balloon expansion, if the balloon is expanded multiple times). For example, if the length of the distal tip is 1.0 mm, the tip will return to its "substantially original shape" if the length after balloon expansion is 0.9 to 1.1 mm (+/−10%).

DETAILED DESCRIPTION OF THE INVENTION

Introduction

The present application describes a distal tip for an angioplasty balloon catheter and methods of using the catheter for treating a vessel in a subject. The distal tip is attached to the distal end of a retractable sheath that covers an angioplasty balloon. During an angioplasty procedure, the catheter is inserted into the vessel and the distal end is positioned in the vicinity of the treatment site. The sheath is retracted such that at least a portion of the balloon passes through the distal tip, and the balloon is inflated at the treatment site until the vessel diameter is restored. The balloon is then deflated and retracted back into the sheath. If the vessel needs treatment at multiple sites, it is useful to have a sheath that permits the balloon to be inflated at each site, and permits different lengths of the balloon to be inflated depending on the lesion size, such that the balloon is partially inflated and refracted into the sheath multiple times. However, multiple expansions of the balloon tend to deform conventional flexible tips known in the art. In contrast, the distal tip described herein has optimal elasticity permitting the tip to flare open during balloon expansion, but sufficient elastic memory to restore its original shape after balloon deflation. Because the tip returns to its original shape after multiple balloon expansions, the tip minimizes damage to the vessel when the sheath is advanced in or withdrawn from the vessel. The tip also provides a smooth transition between the balloon and the sheath, and allows the sheath to be more easily retracted into a guide catheter after multiple balloon expansions. Therefore, the tip provides unexpected advantages compared to a tip that does not return to its original shape after multiple balloon expansions. Specific embodiments will now be described.

Elastomeric Distal Tip

The distal tip described herein is made of an elastomeric plastic. The elastomeric plastic is a polymer having viscoelastic properties (i.e., with both viscosity and elasticity). The distal tip can be made of a thermoplastic elastomer comprising copolymers or a mixture of polymers having both thermoplastic and elastomeric properties. Thus, the material comprising the distal tip is capable of being stretched or deformed and returning to substantially its original shape when the stretching or deformation force is removed. In some embodiments, the distal tip comprises a block copolymer. In some embodiments, the distal tip comprises a polyamide-polyether copolymer, for example, a polymer comprising a flexible polyether and a rigid polyamide. In some embodiments, the distal tip comprises a polyether block amide (PEBA). In one embodiment, the elastomeric plastic is made of PEBAX®, such as PEBAX® 4033 SA 01 MED.

In some embodiments, the distal tip comprises an elastomeric plastic with a tensile strength of about 41 MPa to about 50 MPa (megapascals). In some embodiments, the distal tip comprises an elastomeric plastic having a flexural modulus of between about 0.04 and about 0.10 GPa (gigapascals). It is understood that the distal tip can be made of any elastomeric plastic having the indicated tensile strength and flexural modulus. In some embodiments, the elastomeric plastic of the distal tip has a thickness of about 140 microns to 191 microns (about 0.0055 to 0.0075 inches).

Figure 1B:
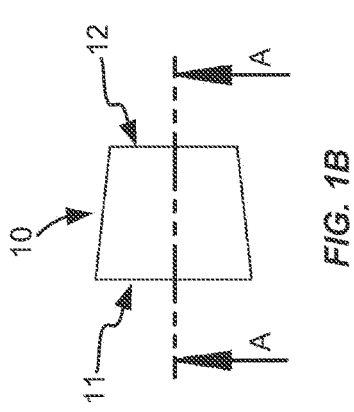
FIG. 1(B) shows a side view.
Figure 1C:
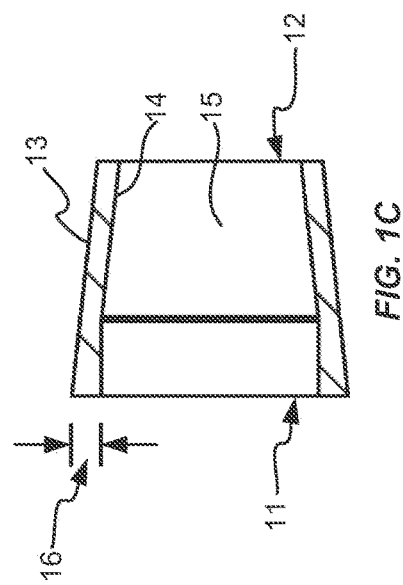
FIG. 1(C) shows a section (A-A) view.

Referring now to FIG. 1, a representative embodiment of the elastic distal tip will be described. As shown in FIGS. 1A and 1B, the distal tip (10) is frustroconical in shape (i.e., the shape of a frustum of a cone), having a larger diameter proximal end (11) and a smaller diameter distal end (12). As shown in FIG. 1C, the tip comprises an outer surface (13) and an inner surface (14) defining a lumen (15). The distance between the outer surface (13) and the inner surface (14) defines a wall thickness (16) of the tip. In some embodiments, the distance between the outer surface (13) and inner surface (14) is between about 0.0075 and 0.0055 inches (about 190 to about 140 microns). In some embodiments, the wall thickness at the proximal end (11) of the tip is thicker than the wall thickness at the distal end (12) of the tip. In some embodiments, the wall thickness at the proximal end is 0.0075 inches (190 microns) and the wall thickness at the distal end is 0.0055 inches (140 microns). In some embodiments, the distal tip is about 1.0 mm to about 1.5 mm in axial length.

In some embodiments, the lumen (15) defined by the inner surface (14) of the tip has a diameter (also referred to as the "inside diameter" of the tip) of between about 0.049 and 0.055 inches at the proximal end, and between about 0.039 and 0.046 at the distal end. In some embodiments, the tip has an inside diameter of about 0.049 inches at the proximal end, and about 0.039 inches at the distal end. In one embodiment, the tip has an inside diameter of about 0.055 inches at the proximal end, and about 0.046 inches at the distal end. In some cases, the lumen of the distal tip has an inside diameter that is at least 0.010 inches less than the inside diameter of the marker band (e.g., at least 0.010, 0.011, 0.012, 0.013, 0.015, 0.016, 0.017, 0.018, 0.019 or 0.020 inches less than the inside diameter of the marker band). In some cases, the inside diameter of the lumen of the distal tip is about 0.010 to about 0.020 inches less than the inside diameter of the lumen of the marker band.

The outer diameter of the tip is the sum of the lumen diameter and the wall thickness, e.g., about 0.0565 inches (0.049 plus 0.0075) to about 0.0625 inches (0.055 plus 0.0075) at the proximal end, and about 0.0445 to about 0.0515 inches at the distal end. The lumen (15) is configured to receive a guide wire and a balloon in its uninflated or unexpanded state.

Outer Shaft with Retractable Sheath

Figure 2:
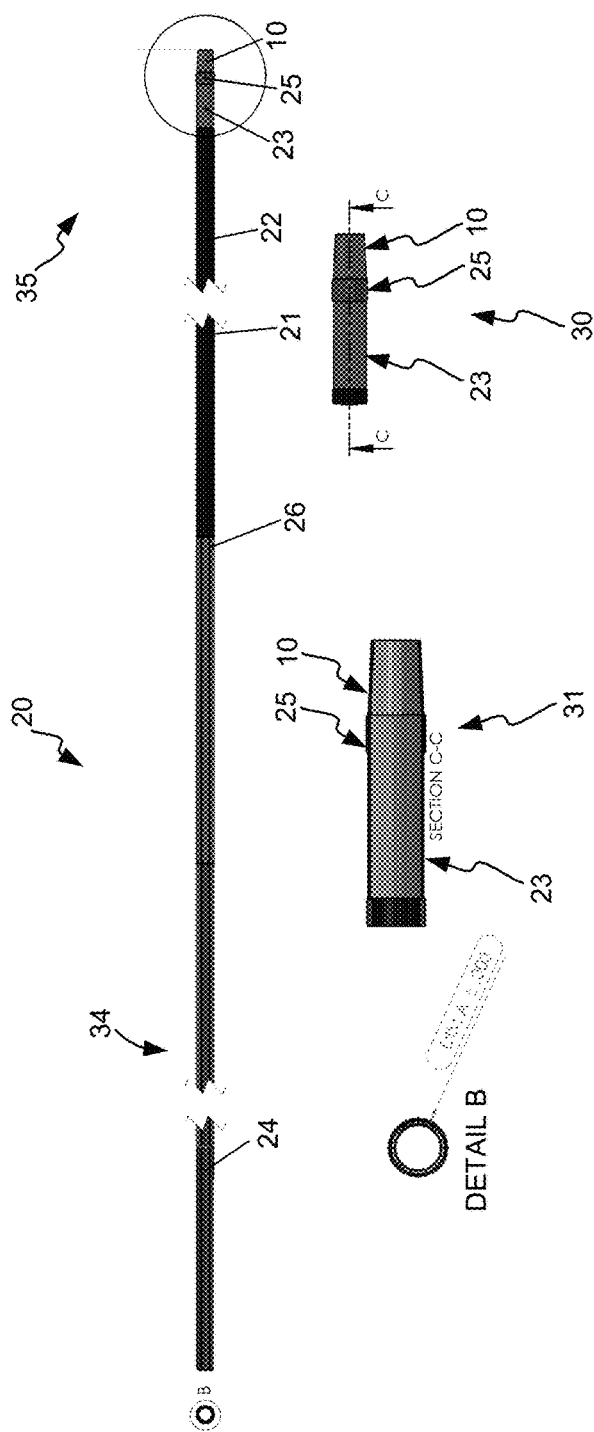
FIG. 2 illustrates one embodiment of a retractable sheath assembly described herein.

Referring now to FIG. 2, a representative embodiment of an outer shaft assembly comprising the elastic distal tip will be described. As shown in FIG. 2, the outer shaft assembly (20) comprises a distal portion (35) comprising a retractable outer sheath (22) that is attached to the distal tip (10). In some embodiments, the outer sheath (22) is a braided shaft made of Grilamid® L25, SS flat wire, and Tri-layer (High Density Polyethylene (HDPE), Plexar, and Grilamid® L25). In some embodiments, retractable outer sheath (22) comprises a mid-shaft tubing (23) that is internal to and surrounded by the braided shaft of the sheath. In some embodiments, the mid shaft tubing (23) is made of a heat and UV stabilized nylon such as Grilamid® L25.

The distal end of the retractable sheath (22) can further comprise an annular marker band (25) made of a radiopaque material disposed proximal to the elastic tip (10). In some embodiments, the marker band (25) comprises platinum. In one embodiment, the marker band is made out of an alloy of platinum and iridium, such as but not limited to an alloy comprising 90% platinum and 10% iridium. The ratio of platinum to iridium in the alloy can be changed based on the desired properties of the marker band. In some embodiments, the marker band is about 0.01 to about 0.10 inches in axial length, for example about 0.01, 0.02, 0.03, 0.04, 0.05, 0.06, 0.07, 0.08, 0.09, or 0.10 inches in axial length. In one embodiment, the marker band is about 0.04 inches in axial length. The marker band has an inside diameter that is greater than the diameter of the balloon in its uninflated configuration. The marker band is resistant to the forces exerted by the balloon when it is inflated, and therefore helps prevent the balloon from expanding proximal to the distal tip. The marker band is also configured to help prevent the distal tip from over-expanding when the balloon is inflated.

In the embodiment shown in FIG. 2, the marker band (25) is concentrically disposed around the circumference of the retractable outer sheath (22) and abuts the proximal end (11) of the distal tip (10). As shown in the detail of the distal end (30) of the outer shaft (20), in some embodiments, the interior diameter of the marker band (25) is substantially the same or similar to the interior diameter of the outer sheath (see section C-C (31)). In some embodiments, the inside diameter of the marker band is greater than the inside diameter of the lumen of the distal tip, e.g., at least 0.010, 0.011, 0.012, 0.013, 0.015, 0.016, 0.017, 0.018, 0.019, or 0.020 inches greater than the inside diameter of the lumen of the distal tip. In some cases, the inside diameter of the marker band is about 0.010 to about 0.020 inches greater than the inside diameter of the lumen of the distal tip. In some embodiments, the marker band is embedded in the material of the retractable sheath. For example, the marker band can be coated on both the exterior and interior surfaces with the material used to construct the sheath. In some embodiments, the braided shaft of the outer sheath (22) does not extend all the way to the distal end of the outer shaft (20). For example, as shown in section C-C of FIG. 2, the distal end of the braided shaft terminates about 0.197 inches (about 5 mm) from the proximal end (11) of the distal tip (10). In some embodiments the marker band (25) circumferentially surrounds and/or is embedded in the material of the mid-shaft tubing (23).

The outer shaft (20) can further comprise a proximal portion (34) comprising a tubular member (21) that is joined or fused to the proximal end of the distal sheath portion (22). The tubular member (21) has a lumen in communication with the lumen of the distal outer sheath (22). In some embodiments, the tubular member (21) is made of polyimide tubing. In some embodiments, the proximal portion (34) further comprises a hypotube (24) surrounded by a hypotube jacket (26). In some embodiments, the hypotube jacket (26) is made of PEBAX® 72D. The distal end of the hypotube jacket (26) can be attached or fused to the proximal end of tubular member (21). In some embodiments, the outer diameter (DIM A of Detail B in FIG. 2) of the outer shaft (20) is from about 0.062 to about 0.068 inches. In one embodiment, the outer diameter of outer shaft (20) is about 0.062 inches. In another embodiment, the outer diameter of outer shaft (20) is about 0.068 inches.

Balloon Catheter

In order to perform an angioplasty procedure, one needs a catheter to position the balloon at the target location in the vessel. The catheter has a proximal end, a distal end, and an elongate flexible body having a generally tubular shape extending therebetween. An inflatable balloon is disposed at a distal end portion of the catheter. In some embodiments, the balloon catheter further comprises the outer shaft assembly (20) described above. In embodiments described herein, the balloon is surrounded by the distal end portion (35) of the outer shaft (20) described above. For example, in some embodiments, the balloon is at least partially surrounded by the distal portion of the retractable sheath (22), which is positioned concentrically around the balloon. The retractable sheath has a flexible, elastomeric tip (described above) attached to the distal end thereof. In some embodiments, the catheter also has a guide-wire lumen that extends at least partially along the length of the catheter. The catheter can also comprise an inflation lumen that is in fluid communication with the balloon and is used to provide fluid pressure to inflate and expand the balloon.

Figure 3:
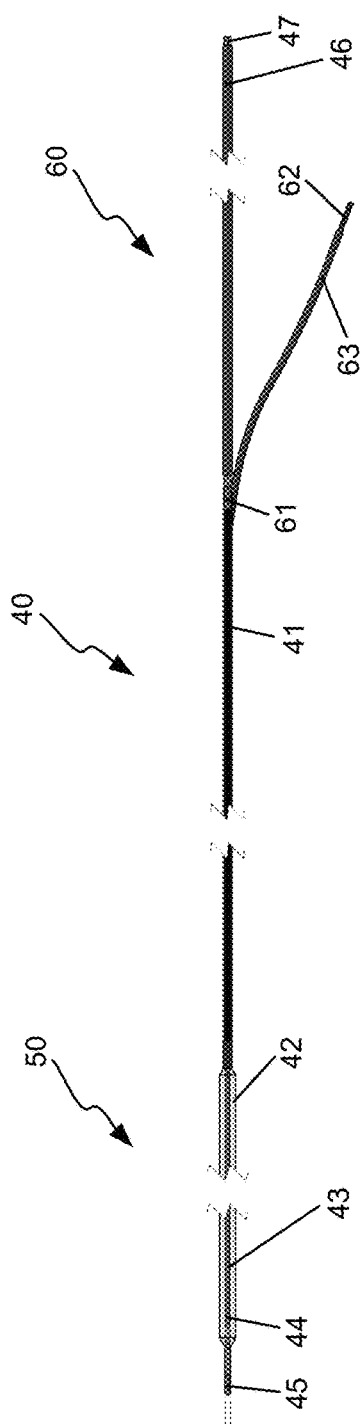
FIG. 3 illustrates one embodiment of a balloon catheter assembly described herein.

Referring now to FIG. 3, a representative balloon catheter (40) will now be described. As shown in FIG. 3, the catheter (40) comprises an axially moveable tubular shaft (41) having an inner lumen and an inflatable balloon (42) attached at the distal end portion (50). The balloon surrounds a tube (43) defining an inner or "inflation" lumen (44). A soft, flexible tip (45) is attached to the distal end of the balloon catheter. The tip (45) is distinct from the elastomeric distal tip (10) described above. The catheter (40) further comprises a proximal end portion (60) comprising a hypotube (46) surrounding a proximal shaft (47) that defines an inner lumen. The inflation lumen (44) surrounded by the balloon is in fluid communication with the lumen defined by the shaft (41) and the lumen defined by the proximal shaft (47). The shaft (41) typically has a second co-axial inner tubing (62) defining a lumen (i.e., "guide wire lumen") that is configured to slidably receive a guide wire. Thus, the shaft (41) can comprise a bilumenal coaxial tube comprising tube (43) and the guide wire tubing (62) disposed within the inflation lumen (44). The guide wire tubing (62) can be surrounded by a shaft or cover (63) that is joined to shaft (41) at the junction (61). The tip (45) can be attached to the distal end of the guide wire to prevent damage to the vessel during insertion of the guide wire into the vessel.

In operation, the tubular shaft (41) is extended in a distal direction such that the balloon (42) or a portion thereof passes through the lumen of the distal tip (10), and the balloon is inflated. After the balloon is deflated, the tubular shaft (41) is retracted in a proximal direction relative to the retractable sheath (22). Alternatively, the retractable sheath (22) is retracted in a proximal direction relative to the balloon, thereby exposing the balloon to the interior of the vessel. The balloon is then expanded to open the vessel, and deflated. The sheath is then pushed distally to cover the balloon.

The balloon catheter can be either an over the wire (OTW) or a rapid-exchange (RX) catheter. The balloon used in the catheter can be either a compliant or non-compliant balloon.

The catheter can further comprise a vascular stent. In some embodiments, the vascular stent is disposed concentrically around the balloon when the balloon is in the uninflated configuration. The stent is generally disposed between the balloon and the retractable sheath.

Methods of Treating a Vessel

The balloon catheter comprising the outer shaft/retractable sheath assembly and elastomeric distal tip described herein is useful for treating a vessel in a subject, for example in a subject suffering from arteriosclerosis or atherosclerosis, or a related disease, such as coronary heart disease, carotid artery disease, peripheral arterial disease, or renal artery disease. The balloon catheter described herein is useful for opening a blood vessel that is partially blocked or occluded by an atheroma or plaque. Because the elastomeric distal tip on the sheath can return to its original shape after multiple balloon expansions, the catheter is especially useful for treating multiple sites in the same or different vessels in the subject. In particular, the distal tip accommodates multiple partial and/or variable length expansions of the balloon without deforming its shape. Methods of treating a vessel in a subject will now be described.

The methods generally comprise inserting a guide catheter into the vessel that needs treatment, passing the balloon catheter through the guide catheter until it exits the distal end of the guide catheter in the vicinity of the treatment site; retracting the retractable sheath in a proximal direction such that at least a portion of the balloon passes through the lumen of the distal tip and comes into contact with the vessel; positioning the balloon at the treatment site; inflating the balloon or portion thereof (for example, by introducing a fluid into the inflation lumen) such that the balloon expands and comes into contact with the vessel wall or with an atheroma (e.g., plaque) deposited in the vessel; expanding the vessel to the desired diameter or further opening the vessel by compressing the atheroma and/or plaque; deflating the balloon; and retracting the deflated balloon back into the sheath through the lumen of the distal tip. The balloon is retracted into the sheath by retracting the balloon shaft in a proximal direction relative to the sheath. Alternatively, the sheath is pushed distally to cover the balloon. If the vessel has more than one anatomical site that needs treatment, the cardiologist can reposition the catheter at the second site, and repeat the above procedure. The procedure can be repeated multiple times at different treatment sites. The length of the balloon that is expanded can be varied depending on the size of the lesion that needs treatment. Because the distal tip maintains its original shape after multiple balloon expansions, trauma to the vessel is reduced when the sheath is pushed distally or retracted proximally in the vessel.

Thus, in some embodiments, the method comprises (a) positioning the balloon catheter in a vessel of the subject; (b) extending an inflatable balloon or a portion thereof through a lumen of the distal tip; (c) expanding the balloon or portion thereof such that the balloon contacts the interior wall of the vessel; (d) deflating the balloon; and (e) retracting the deflated balloon through the lumen of the distal tip, wherein the distal tip returns to its original shape after deflation of the balloon. The balloon is typically expanded to a diameter sufficient to come into contact with at least a portion of the vessel wall or the atheroma or plaque that is blocking the vessel. The balloon is expanded with enough force (e.g., from 1 to 20 atmospheres) to compress the atheroma, thereby increasing the inner diameter of the vessel or the size of the opening in the blockage. If desired, the catheter can be positioned at another treatment site or location in the vessel (e.g., a portion of the vessel having another atheroma), and the above steps repeated one of more times. The distal tip returns to substantially its original shape after each expansion and deflation of the balloon.

The above methods can also be used to deploy a vascular stent in the vessel. For example, a catheter comprising the retractable sheath and distal tip assembly described above can further comprise a stent disposed concentrically around the balloon. The catheter is delivered to the treatment site in the vessel, and the stent is deployed by proximally retracting the sheath and distal tip assembly, such that the stent and balloon pass through the distal tip into the interior of the vessel. The balloon is inflated, thereby expanding the stent from a collapsed or unexpanded configuration to an expanded configuration. After the stent is expanded to the desired diameter, the balloon is deflated and retracted into the sheath through the distal tip. If desired, the catheter is repositioned to another treatment site in the vessel, the sheath is retracted to expose or uncover the balloon or portion thereof (this time without a stent), and the balloon is inflated as above.

EXAMPLES

Example 1

In this example, different tip designs were compared to determine their suitability for returning to their original shape after balloon inflation.

Methods: A catheter assembly with five custom balloon sizes (2.0 mm, 2.5 mm, 3.0 mm, 3.5 mm, and 4.0 mm in diameter when inflated×210 mm in length) was used. The outer sheath assembly was tested by passing the balloon through the lumen of the elastic tip, inflating and deflating the balloons and observing whether or not the elastic tip recovered its original shape after inflating the balloon As shown in Table 1, distal tips comprising different materials were tested for their ability to return to their original shape after balloon inflation.

TABLE 1

| Tip Design # | Materials | Flexural Modulus (Gpa) | Result after balloon inflation |
|---|---|---|---|
| 1. | Tri Layer (HDPE (High Density Polyethylene), Plexar, Grilamid L25) | | |
| | HDPE | 0.500-4.83 | Outer sheath tip does not return to its original shape. |
| | Grilamid L25 | 0.275-0.685 | Outer sheath tip remained expanded after balloon inflation, causing rough transition between balloon and tip of outer sheath. |
| 2. | HDPE | 0.500-4.83 | Outer sheath tip did not subside after balloon inflation, causing uneven transition between balloon and the tip of outer sheath. Outer sheath tip did not return to its original shape. |
| 3. | Pebax 6333 (Polyether Block Amide) | 0.285 | Material was not sufficiently flexible. After deflation of balloon, the outer sheath tip did not return to its original size. |
| 4. | Pebax 5533 (Polyether Block Amide) | 0.170 | Outer sheath tip has smooth transition over the folded balloon. After deflation of balloon, the outer sheath tip only partially returned to its original size. |
| 5. | Pebax 3533 (Polyether Block Amide) | 0.0210 | Material melted easily and it flowed over the mandrel causing the tip to be thinner. |

This example demonstrates that many tip designs are not capable of returning to their original shape after balloon expansion, and therefore do not have the desired properties of the distal tip described herein.

It is understood that the examples and embodiments described herein are for illustrative purposes only and that various modifications or changes in light thereof will be suggested to persons skilled in the art and are to be included within the spirit and purview of this application and scope of the appended claims. All publications, issued patents, and patent applications cited herein are hereby incorporated by reference in their entirety for all purposes.

What is claimed is:

1. An angioplasty balloon catheter comprising an axially moveable retractable sheath and a distal tip attached to a distal end of the sheath,
   where a distal portion of the retractable sheath is positioned concentrically around an inflatable balloon; and
   where the distal tip attached to the distal end of the sheath is an elastomeric plastic having a tensile strength of 41 MPa to 50 MPa, a flexural modulus of between 0.04-0.10 GPa (gigapascals) and a thickness of 140 microns to 191 microns,
   wherein the distal tip is capable of returning to substantially its original shape after expansion and deflation of the balloon.

2. The catheter of claim 1, where the distal tip is an elastomeric plastic comprising a copolymer of polyether and polyamide.

3. The catheter of claim 1, where the distal tip is about 1.0 to 1.5 mm in axial length.

4. The catheter of claim 1, wherein the distal tip is frustoconical in shape and has a greater diameter proximal end and a smaller diameter distal end.

5. The catheter of claim 4, wherein the distal tip tapers in a distal direction.

6. The catheter of claim 4, where the distal tip comprises a lumen extending in a longitudinal direction from the proximal end to the distal end.

7. The catheter of claim 1, wherein the distal tip comprises an annular marker band disposed at the proximal end of the tip.

8. The catheter of claim 7, wherein the marker band has an inside diameter that is greater than an uninflated diameter of the balloon.

9. The catheter of claim 8, wherein the marker band prevents the inflatable balloon from opening.

10. The catheter of claim 7, wherein the marker band is configured to prevent the distal tip from over-expanding.

11. The catheter of claim 7, wherein the marker band is about 0.04 inches in axial length.

12. The catheter of claim 7, wherein the lumen of the distal tip has an axial diameter that is at least 0.010 inches less than the inside diameter of the marker band.

13. The catheter of claim 1, where the retractable sheath comprises an annular marker band made of a radiopaque material disposed proximal to the distal tip.

14. The catheter of claim 13, where the marker band is concentrically disposed around the circumference of the retractable sheath and abuts the proximal end of the distal tip.

15. The catheter of claim 14, wherein the marker band is configured to prevent the distal tip from over-expanding.

16. A method of treating a vessel in a subject, comprising:
(a) positioning the balloon catheter of claim 1 in a vessel of the subject;
(b) extending an inflatable balloon or a portion thereof through a lumen of the distal tip;
(c) expanding the balloon or portion thereof such that the balloon contacts the interior wall of the vessel;
(d) deflating the balloon; and
(e) retracting the deflated balloon through the lumen of the distal tip;
wherein the distal tip returns to its original shape after deflation of the balloon.

17. The method of claim 16, where the catheter is positioned at another location in the vessel without retracting the catheter from the subject, and steps (b)-(e) are repeated, wherein the distal tip returns to its original shape after each deflation of the balloon.

* * * * *